United States Patent [19]
Sluka et al.

[11] Patent Number: 5,248,620
[45] Date of Patent: Sep. 28, 1993

[54] NON-IONIC BLOCK COPOLYMERS OF PROPYLENE OXIDE AND ETHYLENE OXIDE

[75] Inventors: Peter Sluka; Christian Klein, both of Weilheim; Hans-Werner Griesser, Tutzing; Uwe Kobold, Weilheim, all of Fed. Rep. of Germany

[73] Assignee: Boehringer Mannheim GmbH, Mannheim, Fed. Rep. of Germany

[21] Appl. No.: 720,305

[22] Filed: Jun. 25, 1991

[30] Foreign Application Priority Data

Jul. 25, 1990 [DE] Fed. Rep. of Germany ........ 4023671

[51] Int. Cl.$^5$ ........................................... G01N 33/543
[52] U.S. Cl. .................................. 436/531; 436/518; 436/817; 436/826; 435/7.92; 435/7.93; 435/7.94; 435/7.95; 435/962
[58] Field of Search ..................... 435/7.92, 7.93, 7.94, 435/7.95, 962; 436/518, 817, 826, 531

[56] References Cited

U.S. PATENT DOCUMENTS 4,921,808 5/1990 Schneyer et al. ................... 436/503

FOREIGN PATENT DOCUMENTS 0171946 2/1986 European Pat. Off. .
0215457 3/1987 European Pat. Off. .
2111201 6/1983 United Kingdom .
WO-A-
9004179 4/1990 World Int. Prop. O. .

OTHER PUBLICATIONS

Chang et al. Anal. Biochem. 104 102-117 (1980).

*Primary Examiner*—Esther L. Kepplinger
*Assistant Examiner*—Lora Marie Green
*Attorney, Agent, or Firm*—Nikaido, Marmelstein, Murray & Oram

[57] ABSTRACT

The invention concerns a method for the determination of a partner in an immunological reaction based on an immunoassay in which one of the reaction partners is present in a solid phase, wherein a polyethylene oxidepolypropylene oxide block copolymer having the formula I

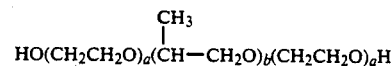

is used as the surface-active agent in which a can have a value between 40 and 150 and b a value between 10 and 50, which is characterized in that a hydrophilic block copolymer composition having the formula I is used which in a 1 % aqueous solution (weight/volume) has a surface tension of at least 45 mN/m and in which the average molar ratio of ethylene oxide groups to propylene oxide groups (2a/b) in the composition is at least 5.8. In addition the invention comprises a reagent for carrying out the above method.

8 Claims, 1 Drawing Sheet

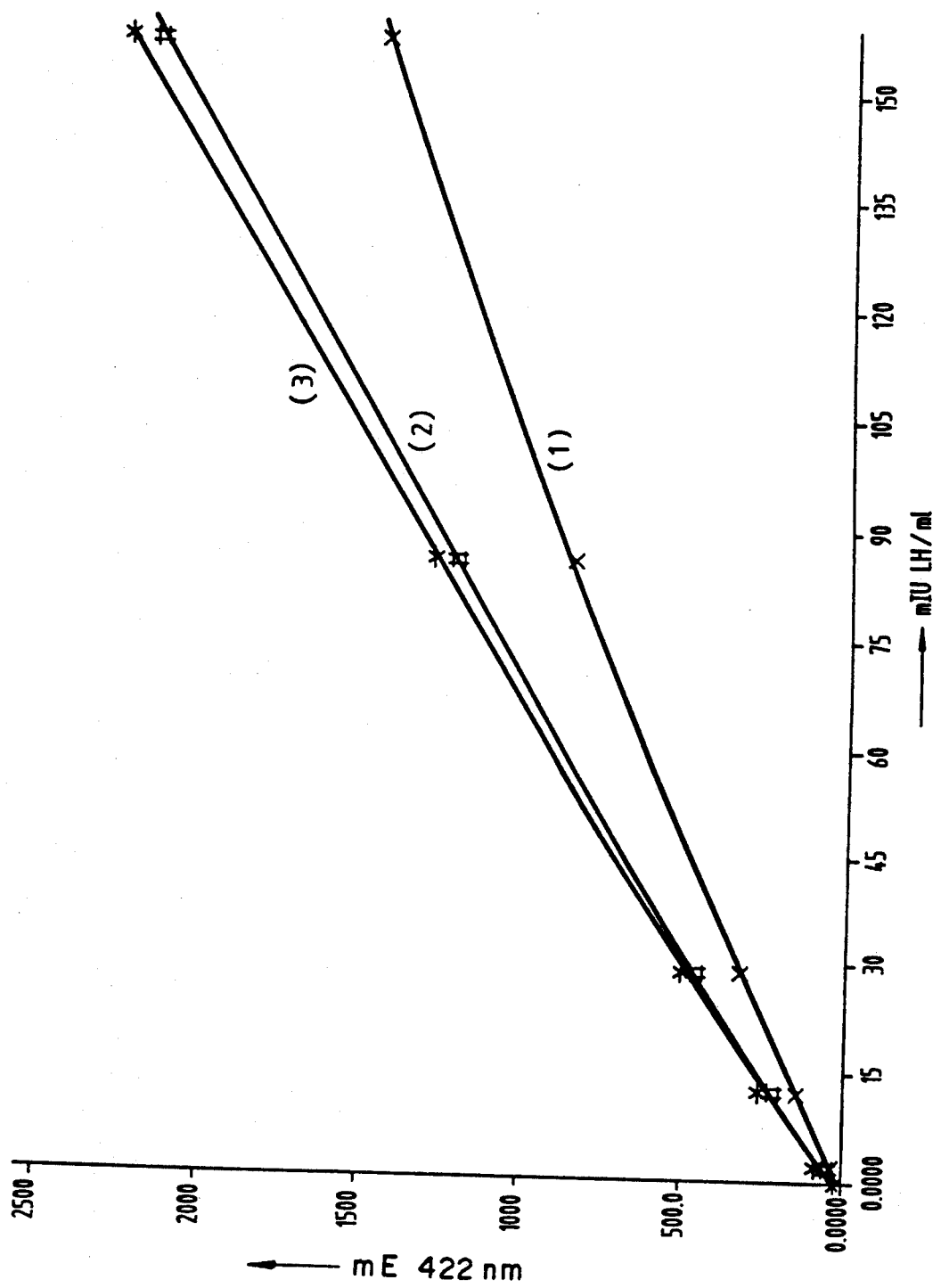

NON-IONIC BLOCK COPOLYMERS OF PROPYLENE OXIDE AND ETHYLENE OXIDE

DESCRIPTION

Non-ionic block copolymers of propylene oxide and ethylene oxide, so-called poloxamers, have already been known for a long time and are widely used as weakly foaming surfactants e.g. as weakly foaming components in cleansing agents, solubilizers, thickening agents, emulsifiers and dispersing agents (see e.g. Ullmanns Enzyklopädie der technischen Chemie, Volume 19, 4th. Edition, published by Verlag Chemie, Weinheim).

The use of these block copolymers as surface-active agents for immunoassays in a heterogeneous phase was disclosed in EP-A 0 215 457.

In an immunoassay in a heterogeneous phase, one of the reaction partners, preferably an antibody, is present bound to a carrier. Various types of methods are known for carrying out the immunological determination in a heterogeneous phase e.g. the sandwich method, the indirect method, the competitive method and further methods which are described in more detail in EP-A 0 215 457.

Unspecific interferences often occur in immunological determinations in a heterogeneous phase which have different causes and which are denoted among others as "matrix effect", "background" and "unspecific binding". In such cases one finds a poor recovery of the substance to be determined, in particular in plasma samples.

According to EP-A 0 215 457 a method for the determination of a partner of an immunological reaction based on an immunoassay at a temperature between 15° and 40° C. is suggested for the reduction of the unspecific binding in which one of the reaction partners is present in a solid phase which is characterized in that a surface-active agent with a HLB hydrophilic/ipophilic balance value of more than 20 is added. Non-ionic block copolymers based on alkylene oxides with 2 to 4 C atoms, in particular compounds having the formula I

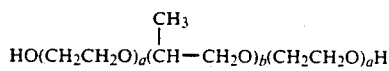

are used as the surface-active agent in which a can have a value between 30 and 150 and b can have a value between 15 and 60. The molar ratio of polyethylene oxide groups to polypropylene oxide groups (2a/b) can thus be between 1 and 20.

The surface-active compound according to formula I can prevent unspecific interactions of particular components of the sample (plasma) with the surface of the reaction vessel during this process and does not lead at the same time to the detachment of the heterogeneous reaction partner i.e. the reaction partner adsorbed at the surface.

Particular types of commercially available poloxamers of the Pluronic series or Synperonic series (manufacturer: BASF or ICI) whose specifications correspond to the required properties are used for heterogeneous immunological test systems according to EP-A 0 215 457. However, it surprisingly turned out that in some tests the recovery of the analyte as well as the gradient of the calibration curve was very much dependent on the production batch of the commercial surfactant used in each case. It was established that only very few selected batches could be used for these tests. Therefore it is necessary in each case to determine the suitability of the individual batches with a complicated function test.

Thus, the object of the present invention was to provide a block copolymer composition having the formula I which is repeatability suitable for use in a heterogeneous immunoassay.

The object according to the present invention is achieved by a method for the determination of a partner in an immunological reaction based on an immunoassay in which one of the reaction partners is present in a solid phase, wherein a polyethylene oxide-polypropylene oxide block copolymer having the formula I

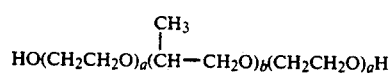

is used as a surface-active agent in which a can have a value between 40 and 150 and b a value between 10 and 50, which is characterized in that a hydrophilic block copolymer composition having the formula I is used which in a 1 % aqueous solution (weight/volume) has a surface tension of at least 45 mN/m and in which the average molar ratio of ethylene oxide groups to propylene oxide groups (2a/b) in the composition is at least 5.8.

The block polymers are not usually present as single chemical compounds but rather as a mixture of several individual compounds each having a different molecular weight and a different molar ratio of polyethylene oxide (EO) groups to polypropylene oxide (PO) groups. For this reason the values a and b are to be understood as average values which can be determined for the mixture from the molecular weight and the molar ratio (EO/PO).

In the case of the method according to the invention it has proven to be favourable to use the surface-active substance, i.e. the hydrophilic block copolymer composition, having the formula I in an amount of 0.1 to 5 % in relation to the weight of the total reaction mixture.

The use of a hydrophilic block copolymer composition according to the present invention is advantageous for the determination of substances in plasma as well as in serum. In both cases an acceleration of the reaction occurs as well as an improved recovery of the substance to be determined in comparison with the use of a conventional commercial block copolymer, in particular when the determinations are carried out in plasma.

The method according to the present invention is applicable to all types of plasma. Thus one can also determine substances in plasma to which EDTA, heparin or citrate has been added for stabilization.

The addition of the hydrophilic block copolymer composition according to the present invention can be carried out for each of the solutions used for the determination. If one for example carries out a determination based on a sandwich method, then an antibody is adsorbed to a carrier material in a first step, whereby after this adsorption step it is expedient to carry out a treatment with a bovine serum albumin solution (to saturate the surface) and subsequently to wash with a salt/detergent solution. In the next step the test solution which contains the substance to be determined and a labelled specific antibody against the complex of antigen and bound first antibody or against parts of this complex, is added. The labelled antibody is preferably conjugated for this with an enzyme, e.g. peroxidase. The amount of antigen, i.e. of the substance to be determined, can be calculated from the amount of labelled antibody bound to the solid phase. In the case of a method according to the present invention the hydrophilic block copolymer is located in the test solution.

The average molar ratio of ethylene oxide groups to propylene oxide groups in a hydrophilic block copolymer composition which is suitable for a method according to the present invention is more than 5.8, i.e. the block copolymer composition contains at least 81.5% by weight ethylene oxide. The term "composition" within the sense of the invention means that the block copolymer, as already set forth above, does not have to be homogeneous but as a rule is composed of several components or fractions with different molecular weights or different molar ratios of ethylene oxide groups to propylene oxide groups. The average molar ratio of ethylene oxide (EO) groups to propylene oxide (PO) groups in the composition is at least 5.8. This means that components or fractions of the block copolymer in which the ratio of EO to PO groups is less than 5.8 can also be present in the composition according to the present invention provided that the molar ratio in the total composition is at least 5.8. However the proportion of fractions with EO/PO <5 should not be more than 25% by weight, preferably not more than 5% by weight of the composition.

It is preferred to use a hydrophilic block copolymer composition having the formula I which in 1% (weight/volume) aqueous solution has a surface tension of 45 to 55 mN/m and in which the average molar ratio of the ethylene oxide groups to the propylene oxide groups (2a/b) is 5.8 to 15. It is preferred that b is more than 15 and particularly preferred that b is not larger than 22. It is preferred that a is between 50 and 70 and particularly preferred that a is between 53 and 63.

A hydrophilic block copolymer composition suitable for a method according to the present invention can be obtained by fractionating a commercial block copolymer wherein this is a compound having the general formula I which in its entirety is not suitable as a surface-active agent in an immunoassay.

Surprisingly it was found that individual hydrophilic fractions of the commercial block copolymer which are completely suitable for the critical tests could be obtained by chromatography of unsuitable batches of a commercial block copolymer having the formula I on a Diaion HP20 column and elution with a water/isopropanol gradient. Mixtures of different suitable fractions could also be used. Examples of suitable commercial block copolymers from which suitable fractions or "compositions" can be isolated are e.g. Synperonic ® PE/F-68 (ICI), Pluronic ® F-68 (BASF), Genapol ® PF80 (Hoechst) and Texadril ® 8780 (Henkel).

In a method according to the present invention it is preferred that a hydrophilic block copolymer composition is used which is essentially free of hydrophobic constituents and in which the molar ratio of ethylene oxide groups to propylene oxide groups (2a/b) is less than 5. Essentially free is understood to mean that a hydrophilic block polymer contains less than 1% and preferably less than 0.5% of hydrophobic constituents which are characterized by a high proportion of propylene oxide groups.

The method according to the present invention has proven to be particularly suitable for the determination of luteinising hormone (LH) or follicle-stimulating hormone (FSH).

The present invention also provides a reagent for carrying out a method according to the present invention which contains a polyethylene oxide-polypropylene oxide block copolymer as the surface-active agent having the general formula I

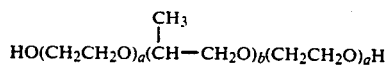

in which the block copolymer composition has a surface tension of at least 45 mN/m in a 1% aqueous solution (weight/volume) and the average molar ratio of ethylene oxide groups to propylene oxide groups (2a/b) in the composition is at least 5.8. The reagent according to the present invention preferably contains one or more suitable fractions of a commercial polyethylene oxide-polypropylene oxide block copolymer having the general formula I.

In order to carry out the method according to the present invention a reagent is used which can contain mobile or/and immobilized partners of the immunological reaction and in addition the usual constituents. It is expedient that it also contains buffer substances e.g. phosphate buffer, citrate buffer, borate buffer and such or/and bovine serum albumin or/and preservatives. If an enzyme is used as the label in the immunological reaction, then the reagent also contains a system for the detection of the enzyme activity.

Using the method according to the present invention and reagent it is possible to improve the recovery in immunoassays carried out in a heterogeneous phase compared to a method in which a commercially obtainable block polymer having the formula I is used.

The following examples and the figure elucidate the invention further:

BRIEF DESCRIPTION OF THE DRAWINGS

FIG. 1 shows calibration of the curves LH test with unfractionated surfactant (1), reference batch (2) and fractionated surfactant, fraction 5 (see Table 1) (3).

EXAMPLES

Example 1

Surfactant fractionation

The surfactant Synperonic ® PE/F-68 (manufacturer: ICI, polypropylene oxide-polyethylene oxide block copolymer) was not suitable in the form supplied by the manufacturer for application in the enzyme-immunoassay for the detection of luteinising hormone (LH) and follicle-stimulating hormone (FSH). A 40% (w/v) aqueous solution of the surfactant was applied to a column with the 5-fold volume of Diaion HP 20 (manufacturer: Mitsubishi Chemicals) and subsequently eluted with a stepped water/isopropanol gradient with an increasing proportion of isopropanol. 3 fractions were collected from each gradient step and the solvent was evaporated. The suitable fractions were eluted at an isopropanol content in the solvent mixture between 20 and 40%. 12 fractions were obtained altogether which were subsequently characterized and evaluated in the function test according to example 2. The analytical data for the fractions are shown in Table 1.

For the purpose of comparison the analytical data are shown for a reference batch of a block copolymer having the general formula I which is suitable for immunological determinations (e.g. for the determination of LH and FSH):

| EO/PO | surface tension | $MM_n$ | b | a |
|---|---|---|---|---|
| 6.21 | 45.2 | 5700 | 17 | 53 |

TABLE 1

Analytical data on the fractionation of the unsuitable batch 13 of Synperonic PE/F-68:

| Fraction | EO/PO | Surface tension (1% sol.) | $MM_n$ | b | a | Proportion by weight (%) |
|---|---|---|---|---|---|---|
| unfractionated | 5.65 | 40.0 | 5800 | 19 | 54 | 100 |
| 1 | 14.43 | 51.8 | | | | 0.8 |
| 2 | — | — | | | | 0.3 |
| 3 | 13.13 | 49.6 | | | | 0.8 |
| 4 | 9.08 | 49.0 | 6500 | 14 | 63 | 11.7 |
| 5 | 7.64 | 48.3 | 5500 | 14 | 53 | 8.8 |
| 6 | 5.82 | 45.2 | 6800 | 22 | 63 | 25.8 |
| 7 | 4.47 | 43.8 | 6800 | 27 | 60 | 22.0 |
| 8 | 4.13 | 38.4 | 6900 | 29 | 59 | 10.1 |
| 9 | 3.65 | 41.2 | 7060 | 32 | 59 | 10.8 |
| 10 | 3.53 | 40.4 | | | | 2.7 |
| 11 | 3.30 | 39.7 | 6500 | 32 | 53 | 5.4 |
| 12 | 2.87 | 38.1 | | | | 0.5 |

EO/PO

Molar ratio of ethylene oxide groups to propylene oxide groups. It is calculated from the signal intensities of the oxymethylene protons and methyl protons in $^1$H-NMR according to the general formula:

$$EO/PO = \frac{I_o - I_M}{I_M} \times 0.75$$

$I_o$ = integral signal intensity of the oxymehtylene protons
$I_M$ = integral signal intensity of the methyl protons The $^1$H-NMR spectra were recorded in $D_2O$ with a Bruker 100 MHz spectrometer.

Surface tension

It was determined in a 1% (w/v) solution of the polymer in redistilled water according to the method of Wilhelmy (C. Weser; GIT Fachzeitschrift für das Laboratorium, 24, 642–648 and 734–742 (1980)). A digital tensiometer of the Krüss Company was used.

$MM_n$

Numerical average of the molemass. It was determined by means of an end-group analysis (C. Ogg, W.L. Porter, C.O. Willits, Ind. Eng. Chem., Anal Ed. 17, 394-7 (1945)).

Proportion by weight

Proportion of the fractions in relation to the total polymer:

$$\frac{\text{weight of the fraction (g)}}{\text{weight of the polymer used (g)}} \times 100$$

The fractions 4, 5, 6 and a pool of the fractions 4-6 were tested. The fractions 4, 5 and the pool were completely suitable with respect to the calibration curve and recovery (with an accepted maximum deviation from the reference batch of 10%). Fraction 6 is only partially suitable (calibration curve is too flat) but was fully suitable in the pool.

Example 2

Determination of luteinising hormone (LH) based on a sandwich technique 1.5 ml of a solution containing a monoclonal antibody against LH (EP-A 0 193 881) at a concentration of 1.5 μg/ml in coating buffer (0.04 mol/1 sodium dihydrogenphosphate, pH 7.4) are dispensed into plastic tubes and incubated for 24 hours at room temperature. Subsequently they are incubated with a solution of 1% bovine serum albumin in 0.9% NaCl for 30 min at room temperature. After washing and drying, 100 μl sample (serum or LH standard solution with 0-25 mU LH/ml, standardized according to the first IRP standard for LH code 68/40, first IRP = first international reference preparation of the WHO) is dispensed into each tube together with 1 ml of a working solution and incubated for 120 min. This working solution contains an anti-LH-peroxidase conjugate (80 mU/ml conjugate of antibody according to EP-A-0 193 881 and peroxidase) in 0.04 mol/1 phosphate buffer, pH 7.4, block polymer according to Example 1 (6 g/1) and PEG 40000 (10 g/1).

After washing with the washing buffer (0.9% NaCl, 0.1% Tween 20) a solution consisting of 100 mmol/1 phosphate/citrate buffer, pH 4.4, 3.2 mmol/1 sodium perborate and 1.9 mmol/1 ABTS® (2,2-azino-bis-(3-ethylbenzathiazoline-6-sulfonic acid)diammonium salt) is added and, after incubating for one hour, the absorbance is determined at 422 nm. The results are shown in FIG. 1 and Table II. The recovery as well as the sensitivity of the determination are improved by the fractionation.

TABLE II

Recovery of LH in sera

| | LH nIU/ml | suitable reference batch | Recovery Batch suitable fractions of a non-fractionated unsuitable batch (fractions 4 + 5 + 6) | unsuitable total batch 13 (without fractionation) |
|---|---|---|---|---|
| Control serum 1 | 94.4 | 100% | 95% | 111% |
| Control serum 2 | 13.5 | 100% | 101% | 120% |
| Human serum 1 | 21.7 | 100% | 99% | 118% |
| Human serum 2 | 25.5 | 100% | 100% | 118% |
| Human serum 3 | 2.3 | 100% | 89% | 136% |

We claim:

1. A method for the determination of an analyte in a sample comprising (i) mixing said sample and a specific binding partner of said analyte immobilized on a solid phase in the presence of a surfactant, which is a composition comprising at least one polyethylene oxide-polypropylene oxide block copolymer having the formula I

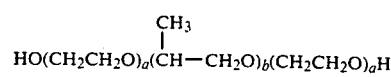

in which a can have a value between 40 and 150 and b a value between 10 and 50, to form a hydrophilic block copolymer composition which composition, in a 1% aqueous solution (weight/volume) has a surface tension of at least 45 mN/m, and in which the average molar ratio of ethylene oxide groups to propylene oxide groups (2a/b) in the composition is at least 5.8 to form a complex, and (ii) detecting said complex on said solid support.

2. A method as claimed in claim 1, wherein in a 1% aqueous solution (weight/volume), said hydrophilic block copolymer composition has a surface tension of 45 to 55 mN/m and the average molar ratio of ethylene oxide groups to propylene oxide groups (2a/b) in said hydrophilic block copolymer composition is 5.8 to 15.

3. A method as claimed in claim 1, wherein b is not more than 22.

4. A method as claimed in claim 1 wherein is between 50 and 70.

5. A method as claimed in claim 1, wherein said hydrophilic block copolymer composition comprises one or several hydropholic fractions of a commercial block copolymer having the formula I.

6. A method as claimed in claim 5, wherein the commercial block copolymer is separated chromatographically by fractionation.

7. A method as claimed in claim 1, wherein said hydrophilic block copolymer composition is essentially free of components in which the molar ratio of ethylene oxide groups to propylene oxide groups (2a/b) is less than 5.

8. A method as claimed in claim 1 for the determination of luteinising hormone (LH) or follicle-stimulating hormone (FSH).

* * * * *